United States Patent [19]
Liversidge et al.

[11] Patent Number: 5,302,401
[45] Date of Patent: Apr. 12, 1994

[54] METHOD TO REDUCE PARTICLE SIZE GROWTH DURING LYOPHILIZATION

[75] Inventors: Gary G. Liversidge, West Chester; Christopher P. Phillips, Brandamore, both of Pa.; Kenneth C. Cundy, Belmont, Calif.

[73] Assignee: Sterling Winthrop Inc., New York, N.Y.

[21] Appl. No.: 987,879

[22] Filed: Dec. 9, 1992

[51] Int. Cl.$^5$ .............................................. A61K 9/51
[52] U.S. Cl. .................................... 424/501; 424/9; 424/489; 424/499; 514/171; 514/777; 514/788; 514/951
[58] Field of Search .................. 424/9, 489, 499, 501; 514/171, 777, 788, 951

[56] References Cited

U.S. PATENT DOCUMENTS 5,145,684  9/1992  Liversidge et al. .................. 424/489

FOREIGN PATENT DOCUMENTS 0193208  9/1986  European Pat. Off. .

*Primary Examiner*—Thurman K. Page
*Assistant Examiner*—Jyothsna Venkat
*Attorney, Agent, or Firm*—William J. Davis

[57] ABSTRACT

This invention discloses a composition comprised of nanoparticles having a surface modifier adsorbed on the surface thereof and a cryoprotectant associated therewith, which cryoprotectant is present in an amount sufficient to form a nanoparticle-cryoprotectant composition. A preferred surface modifier is polyvinylpyrrolidone, and a preferred cryoprotectant is a carbohydrate such as sucrose. This invention further discloses a method of making nanoparticles having a surface modifier adsorbed on the surface and a cryoprotectant associated therewith, comprised of contacting said nanoparticles with the cryoprotectant for a time and under conditions sufficient to form a nanoparticle-cryoprotectant composition.

4 Claims, No Drawings

METHOD TO REDUCE PARTICLE SIZE GROWTH DURING LYOPHILIZATION

FIELD OF THE INVENTION

This invention relates to therapeutic and diagnostic compositions with a cryoprotectant, and to a method for the preparation thereof.

BACKGROUND OF THE INVENTION

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm).

As a result of their small size, lyophilization of therapeutic and diagnostic agents in nanoparticulate form stabilized by a surface modifier (surfactant) is difficult. Conventional lyophilization results in substantial growth of particle size, rendering the resulting particles unusable thus losing the desirable properties provided by rapid dissolution of small drug particles. The present invention describes the application of lyophilization to preparation of freeze-dried drug nanoparticles that retain their small particle size and can be readily redispersed.

This invention is directed to novel compositions that allow lyophilization of nanoparticles with reduced or no particle size growth. These compositions provide for an addition of cryoprotectants to nanoparticles such that the nanoparticles do not agglomerate during lyophilization. This invention is also directed to a method of making such compositions.

SUMMARY OF THE INVENTION

This invention is directed to a composition comprised of nanoparticles having a surface modifier adsorbed on the surface thereof and a cryoprotectant associated therewith, which cryoprotectant is present in an amount sufficient to allow the nanoparticles to be lyophilized.

This invention further discloses a method of making nanoparticles having a surface modifier adsorbed on the surface thereof and a cryoprotectant associated therewith, said method comprising contacting said nanoparticles with the cryoprotectant for a time and under conditions sufficient to allow the nanoparticles to be lyophilized.

DETAILED DESCRIPTION OF THE INVENTION

This invention is directed to a composition comprised of nanoparticles having a surface modifier adsorbed on the surface thereof and a cryoprotectant associated therewith, which cryoprotectant is present in an amount sufficient to allow the nanoparticles to be lyophilized.

The nanoparticles useful in the practice of this invention include a surface modifier. Surface modifiers useful herein physically adhere to the surface of the x-ray contrast agent but do not chemically react with the agent or itself. Individually adsorbed molecules of the surface modifier are essentially free of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants.

Representative examples of surface modifiers include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens TM, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the *Handbook of Pharmaceutical Excipients*, published jointly by the American Pharmaceutical Association and The Pharmaceutical Society of Great Britain, the Pharmaceutical Press, 1986.

Preferred surface modifiers include polyvinylpyrrolidone, tyloxapol, poloxamers such as Pluronic TM F68 and F108, which are block copolymers of ethylene oxide and propylene oxide, and poloxamines such as Tetronic TM 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT TM, which is a dioctyl ester of sodium sulfosuccinic acid, available from American Cyanamid, Duponol TM P, which is a sodium lauryl sulfate, available from DuPont, Triton TM X-200, which is an alkyl aryl polyether sulfonate, available from Rohm and Haas, Tween 80, which is a polyoxyethylene sorbitan fatty acid ester, available from ICI Specialty Chemicals, and Carbowax TM 3350 and 934, which are polyethylene glycols available from Union Carbide. Surface modifiers which have been found to be particularly useful include Tetronic 908, the Tweens TM, Pluronic F-68 and polyvinylpyrrolidone. A particularly preferred surface modifier is polyvinylpyrrolidone (PVP). Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide
n-heptyl β-D-glucopyranoside;
n-heptyl β-D-thioglucoside;
n-hexyl β-D-glucopyranoside;
nonanoyl-N-methylglucamide;
n-nonyl β-D-glucopyranoside;
octanoyl-N-methylglucamide;
n-octyl β-D-glucopyranoside;
octyl β-D-thioglucopyranoside;
and the like.

The surface modifiers are commercially available and/or can be prepared by techniques known in the art. Two or more surface modifiers can be used in combination.

The nanoparticles useful in the practice of this invention can be prepared according to the methods disclosed in U.S. Pat. No. 5,145,684, whose disclosure is incorporated herein by reference. Briefly, nanoparticles are prepared by dispersing a poorly soluble therapeutic or diagnostic agent in a liquid dispersion medium and wet-grinding the agent in the presence of grinding media to reduce the particle size of the contrast agent to an effective average particle size of less than about 400 nm. The particles can be reduced in size in the presence of a surface modifier.

A general procedure for preparing the particles useful in the practice of this invention follows. The therapeutic or diagnostic agent selected is obtained commercially and/or prepared by techniques known in the art as described above, in a conventional coarse form. It is preferred, but not essential, that the particle size of the coarse therapeutic or diagnostic substance selected be less than about 100 μm as determined by sieve analysis. If the coarse particle size of that agent is greater than about 100 μm, then it is preferred that the coarse particles of the therapeutic or diagnostic agent be reduced in size to less than 100 μm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 10–60% and most preferably 10–30% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm$^3$. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 10–60%, and most preferably 10–30% by weight based on the total weight of the dry particle.

Therapeutic and diagnostic agents useful in the composition of the present invention include those disclosed in U.S. Pat. No. 5,145,684, whose disclosure is incorporated herein by reference. A preferred therapeutic agent is 17-α-pregno-2,4-dien-20-yno-[2,3-d]-isoxazol-17-ol (Danazol).

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 300 nm, and more preferably less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

Lyophilization is the process of freeze-drying a composition to remove excess water. The process involves the sublimation of the frozen water, usually under reduced pressure conditions. The process is well known in the art of lyophilization.

Cryoprotectants (cryoprotective agents or compounds) are agents that protect chemical compounds, cells, or tissues from the deleterious effects of freezing that may accompany lyophilization. In the case of nanoparticles, cryoprotectants protect from the agglomeration caused by the process of lyophilization, namely freeze-drying.

Exemplary cryoprotectants include carbohydrates such as the saccharide sucrose, sugar alcohols such as mannitol, surface active agents such as the Tweens, as well as glycerol and dimethylsulfoxide. A preferred cryoprotectant is a carbohydrate. A preferred carbohydrate is a saccharide or disaccharide. A preferred disaccharide is sucrose.

Cryoprotectants are present in the nanoparticles of the present invention in an amount sufficient to allow the nanoparticles to be lyophilized. Cryoprotectants are present in an amount of 0.5% to 90%, preferably 1–50%, and most preferably in an amount of about 2% to about 25%, based on the total weight of the nanoparticulate suspension.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 400 nm; and separating the particles and optionally the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is generally carried out under aseptic conditions.

This invention further discloses a method of making nanoparticles having a surface modifier adsorbed on the surface and a cryoprotectant associated therewith, comprised of contacting said nanoparticles with the cryoprotectant for a time and under conditions sufficient to form a nanoparticle-cryoprotectant composition. That composition allows the nanoparticles to be lyophilized.

This method involves the preparation of therapeutic or diagnostic nanoparticles, as discussed elsewhere herein, and contacting those nanoparticles with a cryoprotectant. Contacting may be by admixing a suspension of nanoparticles with a solution of cryoprotectant, followed by lyophilization at a temperature and for a time sufficient to effect freeze-drying of the nanoparticle suspension.

The amount of cryoprotectant used in this method is from about 0.5% to about 90%, preferably 1% to 50%, and most preferably from about 2% to about 25% based on the total weight of the nanoparticle suspension.

The following examples further illustrate the invention and are not to be construed as limiting of the specification and claims in any way.

EXAMPLE 1

Nanoparticulate Danazol Dispersions

A nanoparticulate dispersion of Danazol was lyophilized alone and in the presence of various cryoprotectants, namely Tween 80, mannitol and sucrose. The mean particle diameter was initially 185 nm. Unmodified dispersion (1 ml) was lyophilized and reconstituted in the initial volume of water. The resulting dispersion had a mean particle size of 250 nm. The original and reconstituted dispersions were analyzed using a HIAC/ROYCO instrument. The results revealed a significant increase in the number of particles above 10 $\mu$m in the reconstituted dispersion ($>17,500$ vs. $<2000$ in the original dispersion).

Addition of 0.02% Tween 80 or 2% mannitol to the original dispersion, followed by significantly lyophilization and reconstitution, did not significantly decrease the number of larger particles in the reconstituted dispersion. However, addition of 2% sucrose to the initial dispersion led to significantly less particles above 10 $\mu$m (21 7500) in the reconstituted dispersion.

EXAMPLE 2

A solution of Danazol (5% w/w) and polyvinylpyrrolidone (PVP) (1.5% w/w), along with 1.5% and 6.5% PVP alone were used in the experiments described in this Example.

From those three solutions above, a number of 6 mL vials with 1 mL of each (about 10 vials of each solution) were filled and prepared for freeze-drying according to the following cycle:

Prefreezing: +5° C. for one hour.
Freezing: Lower shelf temperature to −45° C. and hold for 2 hours.
Primary Drying: Engage vacuum at 80 microns and raise shelf temperature to −30° C. Hold at these conditions for 16 hours.
Secondary Drying: Decrease vacuum to 40 microns and increase shelf temperature to +25° C. Hold for 7 hours.

The vials were then stoppered automatically inside the dryer.

Upon visual examination of the reconstituted solutions, large particles were observed in all of the vials. Therefore, it was deduced that Danazol with PVP and PVP alone at different concentrations would form large particles or aggregates with these formulations and cycle conditions.

EXAMPLE 3

The samples of Example 2 were further modified with excipients such as a) those that reduce surface tension (surfactants; i.e., Tween 80), b) bulking agents (mannitol) and c) cryoprotectants (sucrose). The freeze-drying cycle was also modified.

Using this strategy, vials were loaded as in the previous Example with:

1) 5% w/w Danazol/1.5 w/w PVP (neat)
2) 1+0.02% w/v Tween 80
3) 1+2% w/v Mannitol
4) 1+2% w/v Sucrose Modifications to the freeze-drying cycle consisted of 1) increasing the duration of freezing from +5° C. to −45° C. from 1 hour to 1.5 hours and 2) all other cycle parameters remained the same.

Upon reconstitution, it was observed that the sucrose containing solution appeared most like the starting material. The others did not. Therefore, the addition of sucrose to the Danazol/PVP solution accomplished what the other excipients could not.

EXAMPLE 4

The following solutions were prepared according to the methods in the above Examples.

1) Danazol (5%), 1.5% PVP (unlyophilized)
2) Danazol (5%), 1.5% PVP (freeze dried)
3) Danazol (5%), 1.5% PVP (freeze dried-2)
4) Danazol (5%), 1.5% PVP, 0.02% Tween 80
5) Danazol (5%), 1.5% PVP, 2% Mannitol
6) Danazol (5%), 1.5% PVP, 2% Sucrose After lyophilization (except for Sample 1), the samples were analyzed by HIAC/Royco. The results are in Table 1. The data presented represents the average number of particles counted having a mean particle above 10 μm, 30 μm, 80 μm and 100 μm, respectively.

TABLE 1

| | \_\_\_μm (x, n = 3)\_\_\_ | | | |
|---|---|---|---|---|
| | 10 | 30 | 80 | 100 |
| 1 | 1122 | 15 | 0 | 0 |
| 2 | 19801 | 978 | 2 | 0 |
| 3 | 17063 | 2153 | 1 | 0 |
| 4 | 18148 | 3071 | 2 | 0 |
| 5 | 19196 | 77 | 0 | 0 |
| 6 | 6368 | 94 | 0 | 0 |

The results indicate that the addition of sucrose to the Danazol/PVP solution substantially reduced particle size growth during lyophilization.

The foregoing specification, including the specific embodiments and examples is intended to be illustrative of the present invention and is not to be taken as limiting. Numerous other variations and modifications can be effected without departing from the true spirit and scope of the present invention.

We claim:

1. A composition comprised of nanoparticles containing 0.1–90% by weight of the therapeutic agent 17α-pregno-2,4-dien-20-yno-[2,3-d]-isoxazol-17-ol and having 99.9–10% by weight polyvinylpyrrolidone as a surface modifier adsorbed on the surface thereof and sucrose as the cryoprotectant associated therewith, which cryoprotectant is present in an amount of 0.5–90% by weight based on the total weight of the composition and sufficient to allow said nanoparticles to be lyophilized.

2. A method of making the composition of claim 1 comprised of contacting said nanoparticles with said cryoprotectant.

3. The method of claim 2 further comprising the step of lyophilizing said nanoparticle-cryoprotectant composition.

4. The method of claim 3 wherein said lyophilization is by freeze-drying.

* * * * *